United States Patent
Kosaku

(10) Patent No.: US 7,691,066 B2
(45) Date of Patent: Apr. 6, 2010

(54) PARACENTESIS NEEDLE HOLDER

(75) Inventor: Hideki Kosaku, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 974 days.

(21) Appl. No.: 10/892,099

(22) Filed: Jul. 16, 2004

(65) Prior Publication Data
US 2005/0059891 A1 Mar. 17, 2005

(30) Foreign Application Priority Data
Jul. 17, 2003 (JP) ............................. 2003-198646

(51) Int. Cl.
*A61B 8/00* (2006.01)
(52) U.S. Cl. ....................... 600/461; 600/459; 600/464; 604/117; 604/272
(58) Field of Classification Search ................. 600/459, 600/461, 464; 604/117, 272
See application file for complete search history.

(56) References Cited

U.S. PATENT DOCUMENTS

| | | | | |
|---|---|---|---|---|
| 5,623,931 A | * | 4/1997 | Wung et al. | .................. 600/461 |
| 5,758,650 A | * | 6/1998 | Miller et al. | ................. 600/461 |
| 5,941,889 A | * | 8/1999 | Cermak | ........................ 606/130 |
| 6,379,307 B1 | * | 4/2002 | Filly et al. | ................... 600/461 |
| 6,475,152 B1 | * | 11/2002 | Kelly et al. | .................. 600/461 |
| 6,743,177 B2 | * | 6/2004 | Ito | .............................. 600/461 |
| 7,087,024 B1 | * | 8/2006 | Pruter | ......................... 600/461 |

FOREIGN PATENT DOCUMENTS

| | | |
|---|---|---|
| JP | 04-180740 | 6/1992 |
| JP | 2003-334191 | 11/2003 |

* cited by examiner

*Primary Examiner*—Brian Casler
*Assistant Examiner*—Amanda Lauritzen
(74) *Attorney, Agent, or Firm*—Oblon, Spivak, McClelland, Maier & Neustadt, L.L.P.

(57) ABSTRACT

A paracentesis needle holder attachable to an ultrasonic probe is provided. The holder includes a needle guide, an adjustment mechanism, and an open/close mechanism. The needle guide includes a first base and a second base and is configured to guide a needle in a plurality of directions between the first and second bases. The adjustment mechanism is provided at the needle guide and configured to adjust spacing between the first base and the second base in accordance with a diameter of the needle. The open/close mechanism is coupled with the needle guide and configured to close the first and second bases so that the needle is guided in one of the directions and to open the first and second bases so that the needle becomes releasable from the holder.

20 Claims, 14 Drawing Sheets

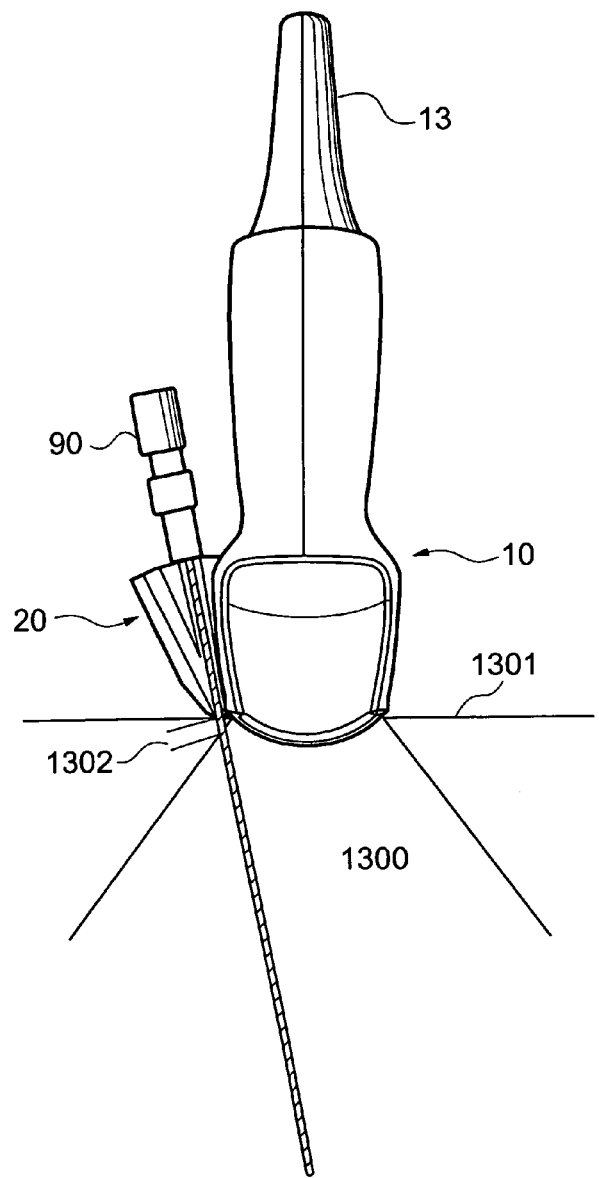
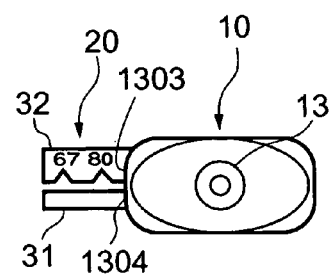
FIG. 13B
FIG. 13A

PARACENTESIS NEEDLE HOLDER

CROSS-REFERENCE TO RELATED APPLICATION

This application is based upon and claims the benefit of priority from prior Japanese Patent Application No. P2003-198646, filed on Jul. 17, 2003, the entire content of which is incorporated herein by reference.

BACKGROUND OF THE INVENTION

1. Field of the Invention

The present invention relates to a paracentesis needle holder which is attachable to an ultrasonic probe. The present invention further relates to an ultrasonic probe having the paracentesis needle holder.

2. Discussion of the Background

A paracentesis operation is conducted with a needle while an operator such as a doctor or a radiological technologist is observing ultrasound images displaying internal conditions of a patient. In the paracentesis operation, the operator, for example, samples patient's tissues such as tumor tissues and injects medical agents into a patient's body. The ultrasound images are typically obtained by an ultrasonic probe specifically manufactured for the paracentesis operation.

Recently, however, a new type of an ultrasonic probe has been introduced. The new type of an ultrasonic probe can be used not only as an ordinary ultrasonic probe but also with an attachable holder of a needle for the paracentesis operation. Such a new type of the ultrasonic probe has been improved in various manners. One example is disclosed in Japanese Patent Application Publication No. PH10-248849. The Japanese Patent Application Publication discloses a needle holder is formed with a plurality of holes to guide a needle in different angles. Another known example is a needle holder with a single hole to guide a needle. The hole can be moved in a predetermined range of angles.

In the above first example, however, it is required to replace the needle holder with another one when a needle in a different size is required in the paracentesis operation.

In the other example mentioned above, the needle holder is likely to be large in size and quite heavy. Therefore, when this needle holder is mounted on an ultrasonic probe, it is difficult for the operator to manipulate the ultrasonic probe during the paracentesis operation.

SUMMARY OF THE INVENTION

According to the first aspect of the present invention, there is provided a paracentesis needle holder attachable to an ultrasonic probe. The holder includes a needle guide, an adjustment mechanism, and an open/close mechanism. The needle guide includes a first base and a second base and is configured to guide a needle in a plurality of directions in between the first and second bases. The adjustment mechanism is provided at the needle guide and is configured to adjust spacing between the first base and the second base in accordance with a diameter of the needle. The open/close mechanism is coupled with the needle guide and is configured to close the first and second bases so that the needle is guided in one of the directions and to open the first and second bases so that the needle becomes releasable from the holder.

According to the second aspect of the present invention, there is provided a paracentesis needle holder attachable to an ultrasonic probe. The holder includes a holder member, a fixed member, a pivoted member, and a handle. The holder member is attachable around the ultrasonic probe. The fixed member is attached to the holder member and is configured to have a needle bearer. The pivoted member is coupled to the fixed member and is configured to have a gutter unit. The pivoted member is biased to the fixed member by a bias member. The handle is attached to the pivoted member and is configured to turn the pivoted member against a force of the bias member and to open the pivoted member and the fixed member. The gutter unit and the needle bearer are configured to face to each other and to guide a needle in a plurality of directions.

According to the third aspect of the present invention, there is provided a paracentesis needle holder for an ultrasonic probe. The holder includes a guide unit, a bear-up unit, and an adjustment mechanism. The guide unit is configured to have a gutter unit with a gutter portion capable of holding a needle at a plurality of angles with respect to the ultrasonic probe. The bear-up unit is coupled to the guide unit and is configured to have a needle bearer with a support member. The gutter portion and the supporter member are configured to securely hold the needle in place when the guide unit and the bear-up unit are closed. The adjustment mechanism is provided to at least one of the guide unit and the bear-up unit and is configured to adjust spacing between the gutter portion and the supporter member when the guide unit and the bear-up unit are closed.

According to the fourth aspect of the present invention, there is provided an ultrasonic probe. The probe includes a main unit and a paracentesis needle holder. The paracentesis needle holder is mounted onto the main unit. The paracentesis needle holder includes a needle guide, an adjustment mechanism, and an open/close mechanism. The needle guide includes a first base and a second base and is configured to guide a needle in a plurality of directions between the first and second bases. The adjustment mechanism is provided at the needle guide and is configured to adjust spacing between the first base and the second base in accordance with a diameter of the needle. The open/close mechanism is coupled with the needle guide and is configured to close the first and second bases so that the needle is guided in one of the directions and to open the first and second bases so that the needle becomes releasable from the holder.

According to the fifth aspect of the present invention, there is provided an ultrasonic probe. The probe includes a main unit, a holder member, a fixed member, a pivoted member, and a handle. The holder member is attached around the main unit. The fixed member is attached to the holder member and is configured to have a needle bearer. The pivoted member is coupled to the fixed member and is configured to have a gutter unit. The pivoted member is biased to the fixed member by a bias member. The handle is attached to the pivoted member and is configured to turn the pivoted member against a force of the bias member and to open the pivoted member and the fixed member. The gutter unit and the needle bearer are configured to face to each other and to guide a needle in a plurality of directions.

According to the sixth aspect of the present invention, there is provided an ultrasonic probe. The probe includes a main unit and a paracentesis needle holder. The paracentesis needle holder is mounted onto the main unit and includes a needle guide and an open/close mechanism. The needle guide includes a first base having a first side and a second base having a second side. The needle guide is configured to guide a needle in at least one direction between the first and second bases. The first and second bases are opposed to each other when the first and second bases are closed. The first and second bases face to the ultrasonic probe at the first and second sides along a proximal end to a distal end of the ultrasonic probe when the first and second bases are closed. The open/close mechanism is coupled with the needle guide and is configured to close the first and second bases so that the needle is guided in one of the at least one direction and to open the first and second bases so that the needle becomes releasable from the paracentesis needle holder.

BRIEF DESCRIPTION OF THE DRAWINGS

A more complete appreciation of embodiments of the present invention and many of its attendant advantages will be readily obtained by reference to the following detailed description considered in connection with the accompanying drawings, in which:

FIG. 13A illustrates an exemplary relationship between the ultrasonic probe, the paracentesis needle holder, a needle, a radiated ultrasound, and a patient's body according to one embodiment;

FIG. 13B is an illustration of the ultrasonic probe having the paracentesis needle holder from a side of a cable according to one embodiment;

DESCRIPTION OF THE EXEMPLARY EMBODIMENTS

Embodiments of a paracentesis needle holder and an ultrasonic probe having a paracentesis needle holder will be described with reference to the accompanying drawings.

Figure 1:
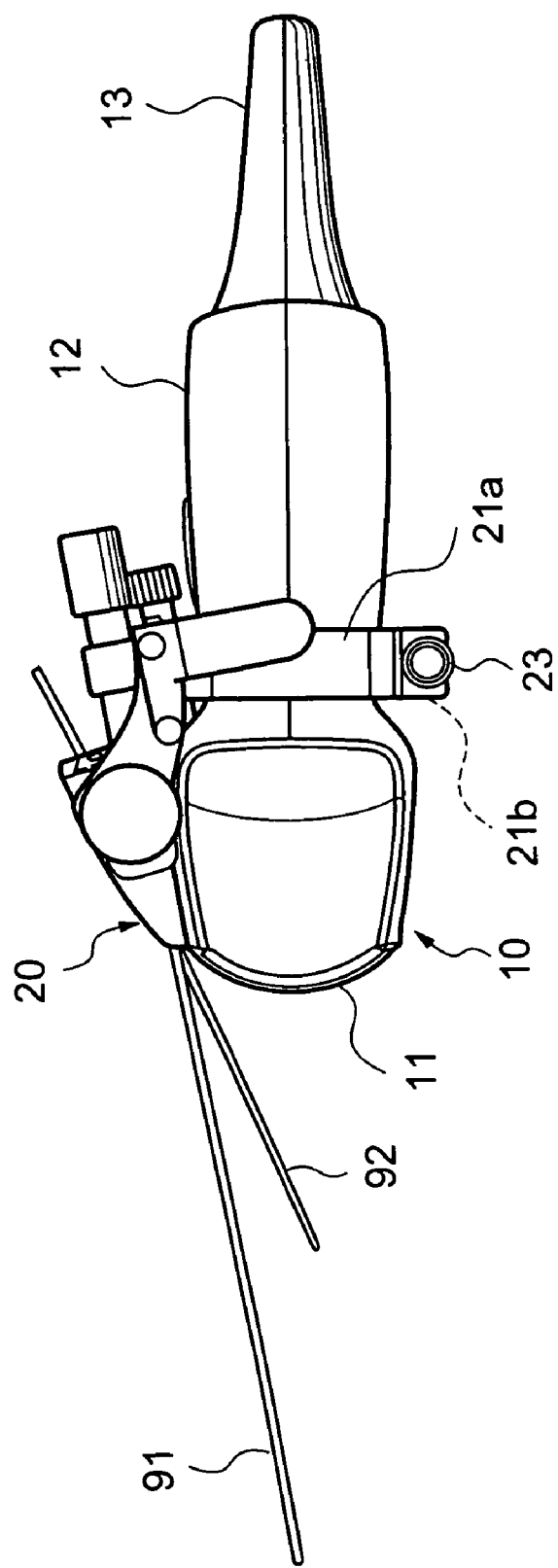
FIG. 1 is an illustration showing an exemplary view from one direction of an ultrasonic probe having a paracentesis needle holder according to one embodiment.
Figure 2:
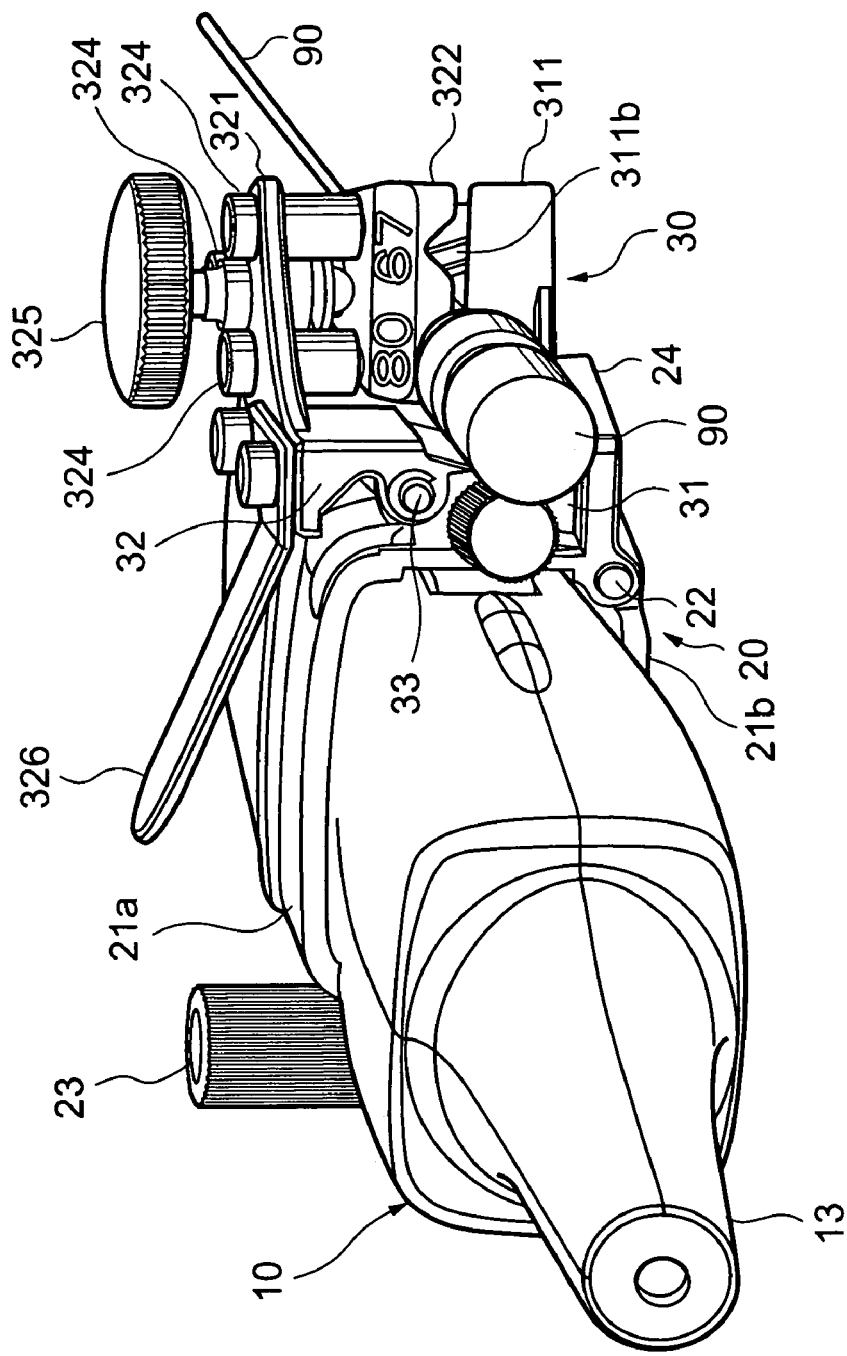
FIG. 2 is an illustration showing another exemplary view from another direction of the ultrasonic probe shown in FIG. 1.
Figure 3:
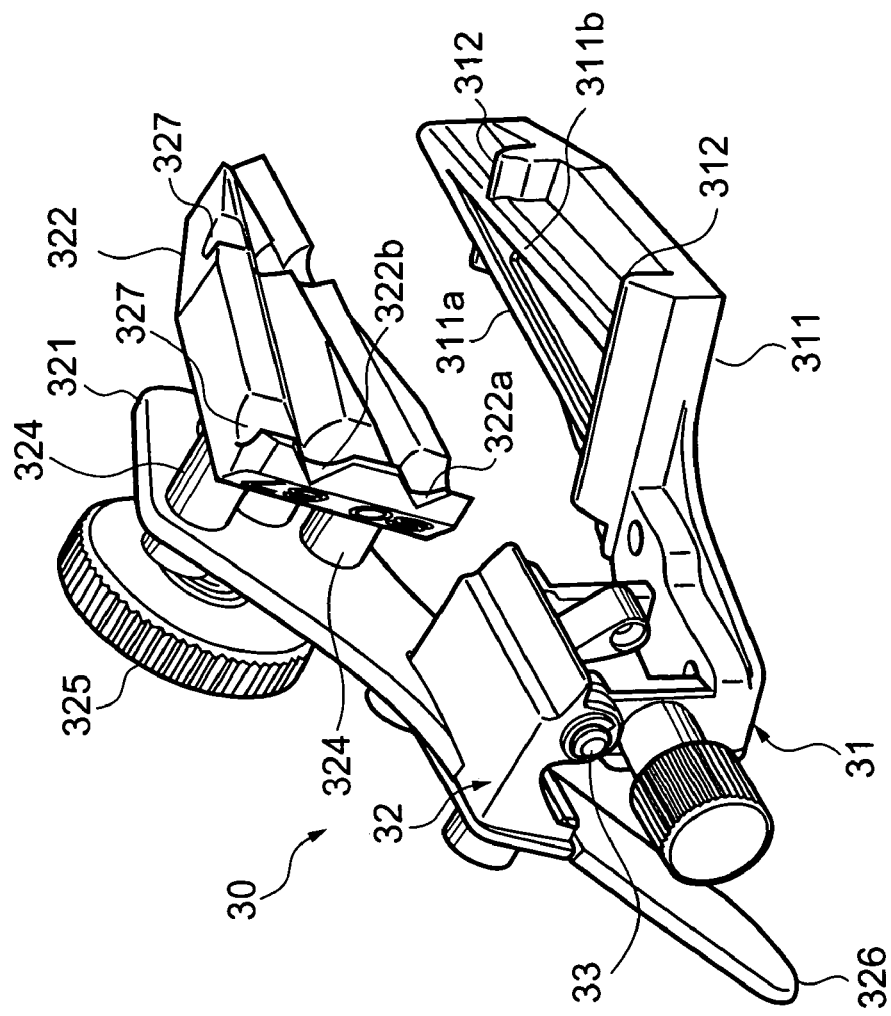
FIG. 3 is an illustration showing an exemplary view of the paracentesis needle holder according to one embodiment.

FIGS. 1 and 2 show an ultrasonic probe having a paracentesis needle holder according to one embodiment. FIG. 3 shows a paracentesis needle holder according to one exemplary embodiment. Precisely, FIG. 1 shows a side view of an ultrasonic probe 10. FIG. 2 shows a perspective view of the ultrasonic probe 10 with a cable 13 from its one end. FIG. 3 shows a paracentesis needle holder 20 without holder members 21a and 21b. Two paracentesis needles (hereinafter referred to as needles) 91 and 92 in different directions or orientations are shown in FIG. 1. This is only for the purpose of explanation. Only one needle 90 is usually used in practice, as shown in FIG. 2.

The ultrasonic probe 10 generates ultrasound beams in an arc form and scans a patient's body. Such a probe is known as a convex type ultrasonic probe. However, other types of an ultrasonic probe such as, for example, a linear scan type and a sector scan type may be used as the ultrasonic probe 10.

The ultrasonic probe 10 includes an acoustic lens 11, a handle body 12, and the cable 13. The acoustic lens 11 is provided at a distal end of the ultrasonic probe 10. When the ultrasonic probe 10 generates ultrasound beams, the acoustic lens 11 is brought in contact with the patient's body to scan the patient's body. The operator typically holds the handle body 12 during the scanning. Since the ultrasonic probe 10 can be a part of an ultrasound diagnosis apparatus (not shown in the drawings), the cable provided at the proximal end of the ultrasonic probe 10 is typically connected to a main unit of the ultrasound diagnosis apparatus.

The ultrasonic probe 10 is equipped with the paracentesis needle holder 20 as shown in FIGS. 1 and 2. The paracentesis needle holder 20 includes the holder members 21a and 21b, which may be made of metals or any other suitable material. The holder members 21a and 21b are coupled by a hinge 22. AS shown in the embodiment in FIG. 2, the holder members 21a and 21b may be a belt strapped around the ultrasonic probe 10. The belt may be attached to the hinge 22. The holder members 21a and 21b strap around the ultrasonic probe 10 so that the paracentesis needle holder 20 is mounted on the ultrasonic probe 10. In one embodiment, the holder members 21a and 21b may have two belts fixed at the other ends by a screw fixer 23. Since there may be a space between the other ends of the holder members 21a and 21b when the holder members 21a and 21b are clipped on the ultrasonic probe 10, the screw fixer 23 is used to further tighten the holder members 21a and 21b around the probe. Accordingly, the holder members 21a and 21b are fixed at their respective another ends (See FIG. 9). The holder members 21a and 21b may be elastic. Due to the elastic behavior, the holder members 21a and 21b may be tightly fixed by the screw fixer 23.

As shown in FIG. 2, the holder member 21a includes a pedestal 24 which protrudes from a portion where the hinge 22 is provided. A needle guide 30 is connected to the pedestal 24. The needle guide 30 includes a bear-up unit 31 (or the second base or a fixed member) and a guide unit 32 (or the first base or a pivoted member). The bear-up unit 31 and the guide unit 32 are coupled by a hinge 33. A base of the bear-up unit 31 may be fixed on the pedestal 24 by a screw fixer, welding, or any other appropriate means. As shown in FIG. 2, the bear-up unit 31 may include a needle bearer 311 horizontally protruding from its base. Although not shown in the drawings, a spring (or a bias member) may be provided at the hinge 33 so that the guide unit 32 is biased towards the bear-up unit 31. The hinge 33 and the spring may be an open/close mechanism.

The guide unit 32 includes a base 321 and a needle gutter unit 322. The base 321 can be configured in a form similar to the letter 'L'. The needle gutter unit 322 is provided at the distal end of the base 321. The distal end may be closer to the needle bearer 311. The needle gutter unit 322 can be moved closer to or away from the needle bearer 311.

The spring causes the needle gutter unit 322 and the needle bearer 311 to be in an open position as shown in FIG. 3. The needle bearer 311 has protrusions or supporters 311a and 311b formed in different directions. In FIG. 3, there are two supporters. The needle bearer 311 may have more supporters in accordance with predetermined angles for the needle 90 in the paracentesis operation. The needle gutter unit 322 includes valley-like grooves or gutters 322a and 322b configured to meet with the supporters 311a and 311b. The supporters 311a and 311b hold the needle 90 inserted through the gutters 322a and 322b in place. When the needle gutter unit 322 is moved towards and meets the needle bearer 311 in to a closed position, there is spacing between the supporters 311a, 311b and the gutters 322a, 322b. The needle 90 can be inserted and guided along one of the gutters 322a and 322b and supported by corresponding one of the supporters 311a and 311b.

The needle gutter unit 322 may be slidably coupled to the base 321 through, for example, three guide members 324. These three guide members 324 may be positioned to form a triangle. An adjustment screw 325 may be provided inside the triangle. The guide members 324 and the adjustment screw 325 may be an adjustment mechanism and will be described in detail later.

On the base 321, a handle 326 is provided which extends from a proximal side of the needle guide 30 with respect to the ultrasonic probe 10 and also in a direction against the surface of the ultrasonic probe 10. Therefore, when the handle 326 is pressed down towards the surface of the ultrasonic probe 10 (or towards the holder member 21a), the guide unit 32 is turned against the bias force around an axis of the hinge 33 so that the needle gutter unit 322 is opened from the needle bearer 311. As a result, the needle 90 guided by one of the gutters 322a and 322b and one of the supporters 311a and 311b can be released from the paracentesis needle holder 30. For example, even during the paracentesis operation, it may be possible to easily release the needle 90 inserted in the patient's body. In other words, the paracentesis needle holder 30 (and the ultrasonic probe 10) can be removed from the needle 90.

On the needle bearer 311, there are one or more convex members 312 as shown in FIG. 3. In a manner corresponding to the convex members 312, there are one or more concave members 327 on a surface of the needle gutter unit 322 as shown in FIG. 3. When the needle gutter unit 322 is moved towards and faces the needle bearer 311, the convex members 312 and the concave members 327 may be engaged so as to ensure alignment between the needle gutter unit 322 and the needle bearer 311.

Figure 4:
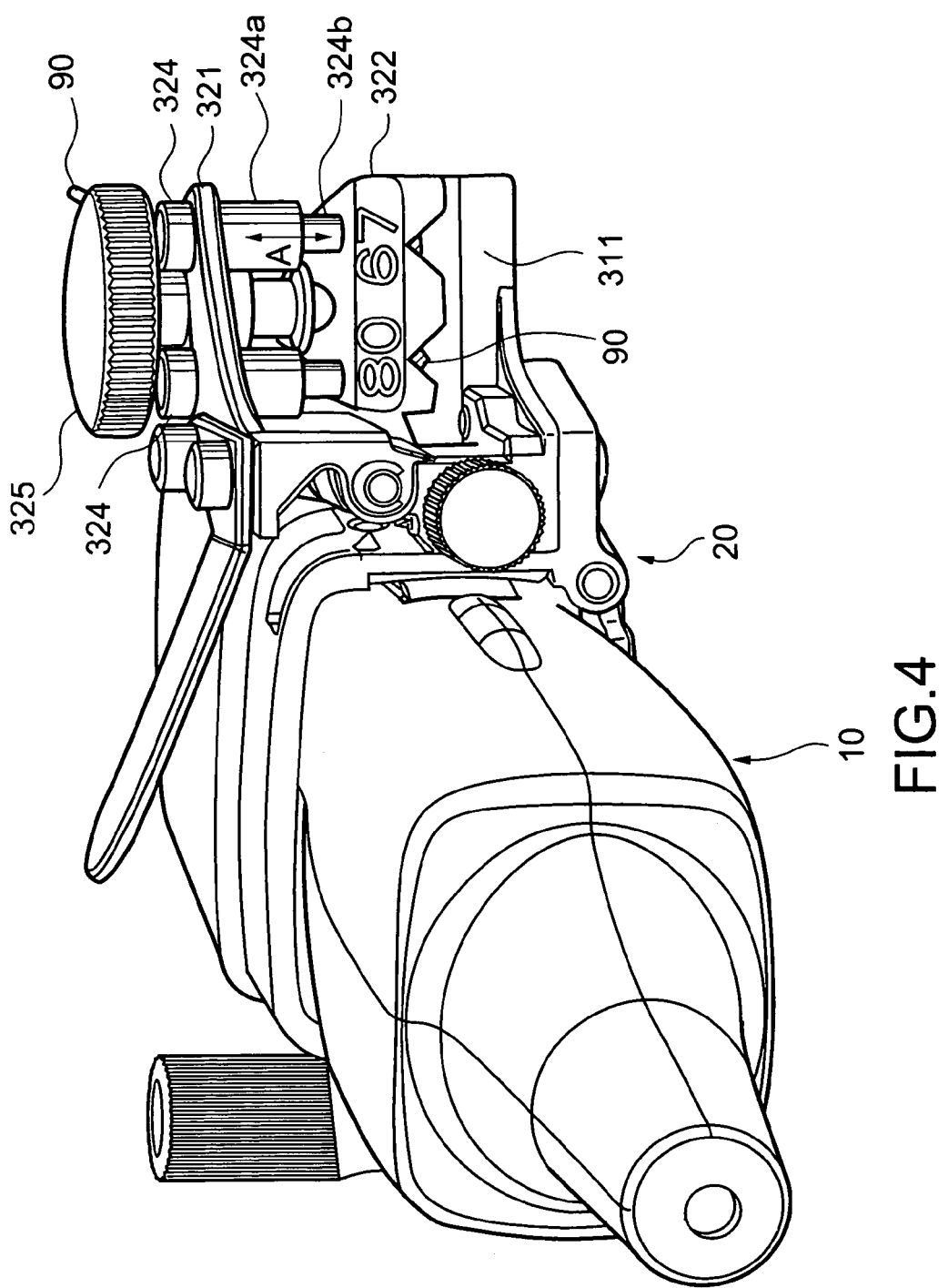
FIG. 4 illustrates the ultrasonic probe having the paracentesis needle holder particularly showing an adjustment screw according to one embodiment.
Figure 5:
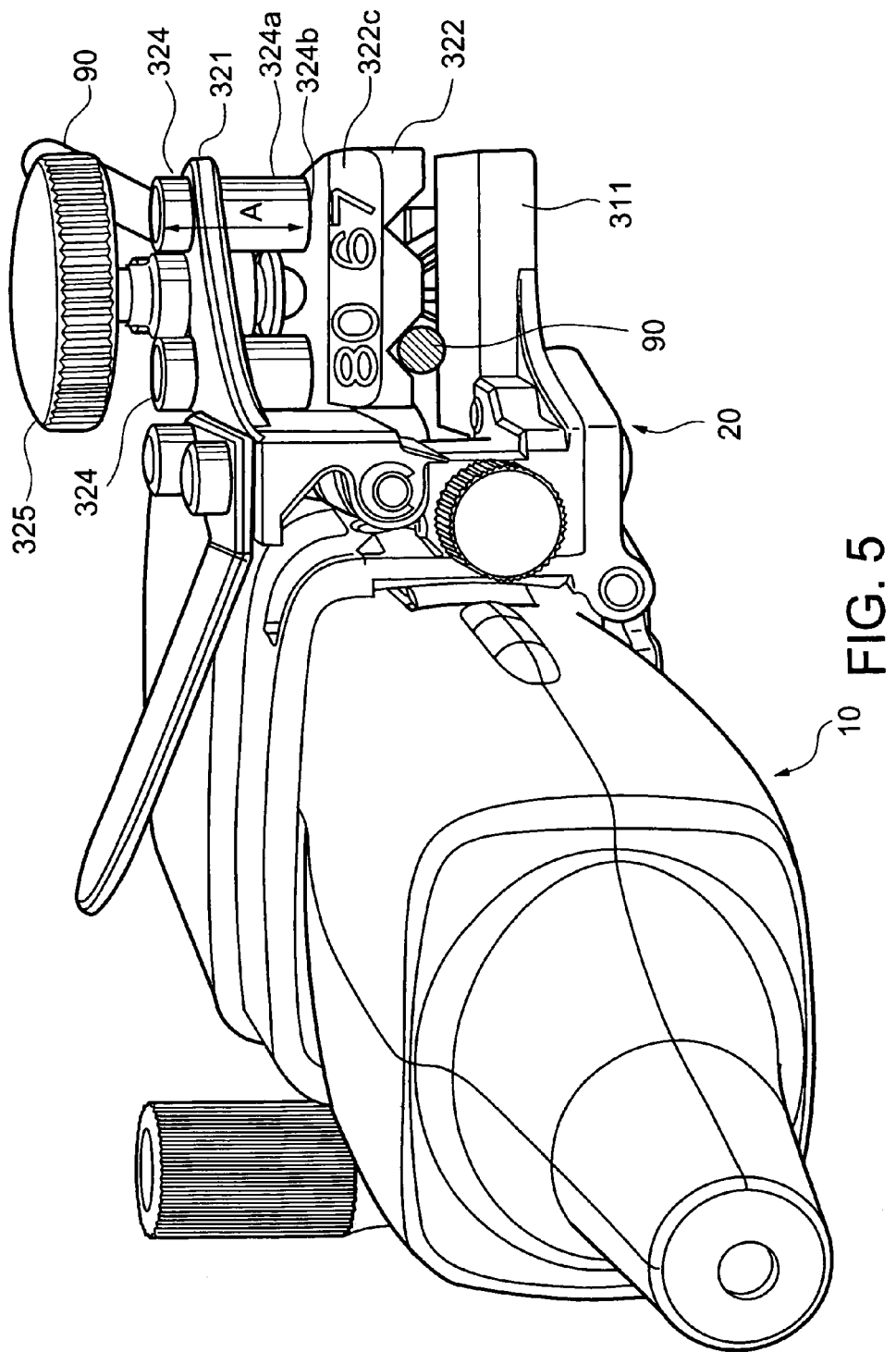
FIG. 5 illustrates the ultrasonic probe having the paracentesis needle holder of FIG. 4 holding a needle.

An adjustment screw 325 will be described with reference to FIGS. 4 and 5. FIG. 4 illustrates the ultrasonic probe 10 having the paracentesis needle holder 20 with an adjustment screw 325 according to one embodiment. Similarly, FIG. 5 illustrates the ultrasonic probe 10 having the paracentesis needle holder 20 with an adjustment screw 325 according to another embodiment. The difference between FIG. 4 and FIG. 5 is only a diameter of the needle 90. The needle 90 in FIG. 4 has a larger diameter than the one in FIG. 5. A top of the needle 90 to be held by the operator is not shown in FIGS. 4 and 5 so that the difference can easily be recognized.

The adjustment screw 325 is rotatably engaged with the base 321 and is also screwed together with the needle gutter unit 322. Accordingly, the base 321 is coupled to the needle gutter unit 322. When the adjustment screw 325 is rotated, the needle gutter unit 322 is moved up or down relative to the base 321 in a direction A. For example, when the adjustment screw 325 is rotated clockwise, the needle gutter unit 322 moves towards the needle bearer 311 or moves away from the base 321. Alternatively, when the adjustment screw 325 is rotated counterclockwise, the needle gutter unit 322 moves towards the base 321 or moves away from the needle bearer 311.

In the above movement of the needle gutter unit 322, the needle gutter unit 322 is guided by the three guide members 324. Each guide member 324 includes a tube member 324a and a rod member 324b. The tube member 324a is fixed to the base 321. The rod member 324b is fixed to the needle gutter unit 322. The rod member 324b is slidably inserted in the tube member 324a. The tube member 324a and the rod member 324b may be telescopically coupled. Therefore, the spacing between the needle gutter unit 322 and the needle bearer 311 can be adjusted in accordance with the thickness (or the diameter) of the needle 90 to be guided by one of the gutters 322a, 322b and corresponding one of the supporters 311a, 311b. A distance between the one gutter 322a (322b) and the one supporter 311a (311b) can be adjusted in accordance with the thickness (or the diameter) of the needle 90 to be guided. The diameter of the needle 90 may be, for example, eleven gauges or twenty-two gauges. In FIG. 4, the needle 90 is small. Therefore, the needle gutter unit 322 is lowered a lot, and the rod member 324b is exposed a lot. On the other hand, in FIG. 5, the needle 90 is large. Therefore, the needle gutter unit 322 is not as much lowered as in FIG. 4, and the rod member 324b is not as much exposed as in FIG. 4.

In the above adjustment, the three guide members 324 help the needle gutter unit 322 to smoothly descend and ascend so as to keep an appropriate distance from the needle bearer 311. As a result, the needle 90 is held in an appropriate pressure to be allowed to move along the gutter 311a (311b).

The operations of the ultrasonic probe 10 and the paracentesis needle holder 20 will be described below. The ultrasonic probe 10 can be used independently from the paracentesis needle holder 20.

Since a scan direction with ultrasound beams is predetermined in the ultrasonic probe 10, the ultrasonic probe 10 is required to be used in consideration of the scan direction. Otherwise, images obtained by the scan are displayed reversely. Therefore, it is necessary to consider a position of the paracentesis needle holder 20 relative to the ultrasonic probe 10 when the paracentesis needle holder 20 is mounted on the ultrasonic probe 10. That is, it is preferable to mount the paracentesis needle holder 20 in accordance with the scan direction.

Figure 6:
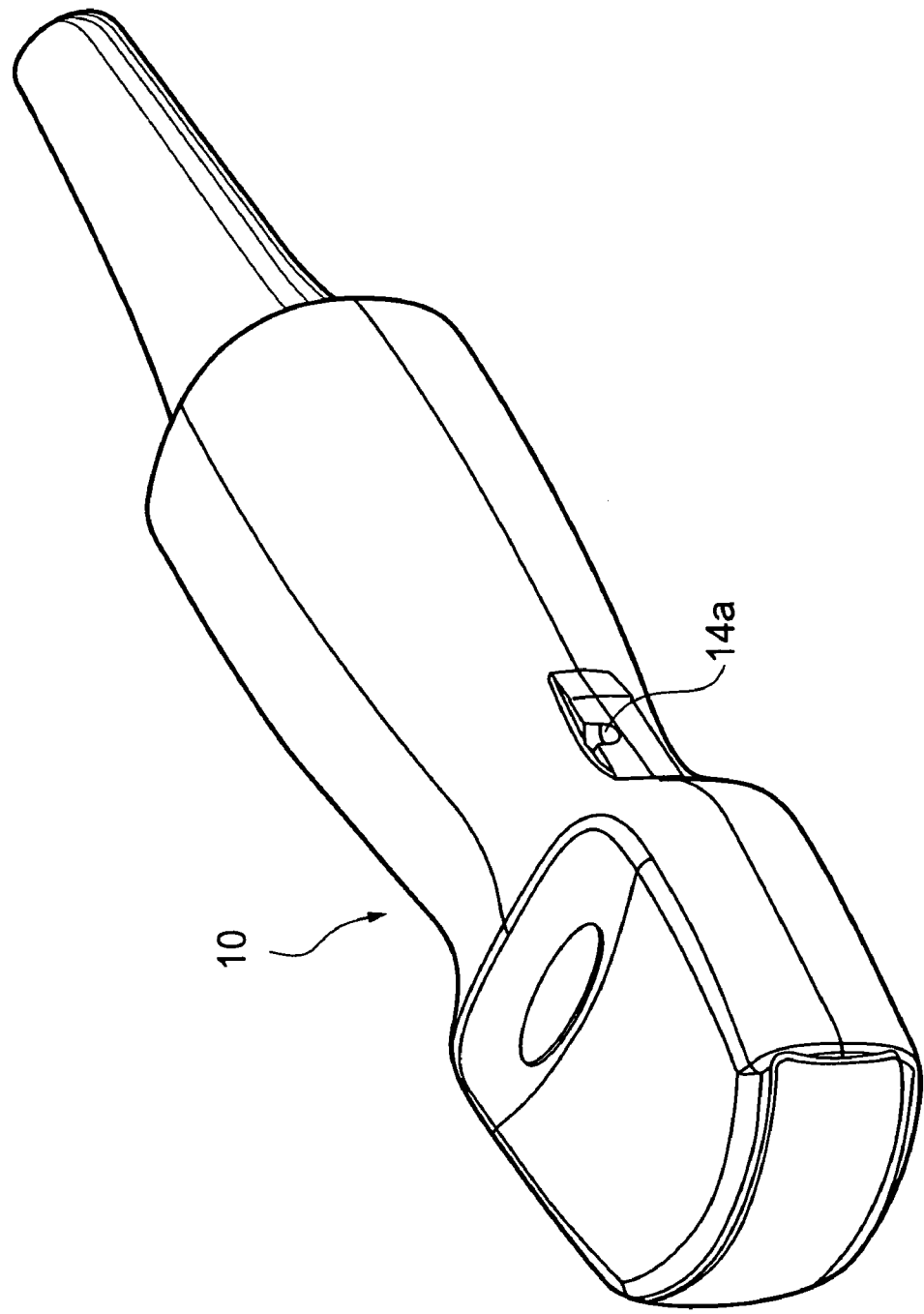
FIG. 6 is an illustration showing an exemplary view of the ultrasonic probe according to one embodiment.
Figure 7:
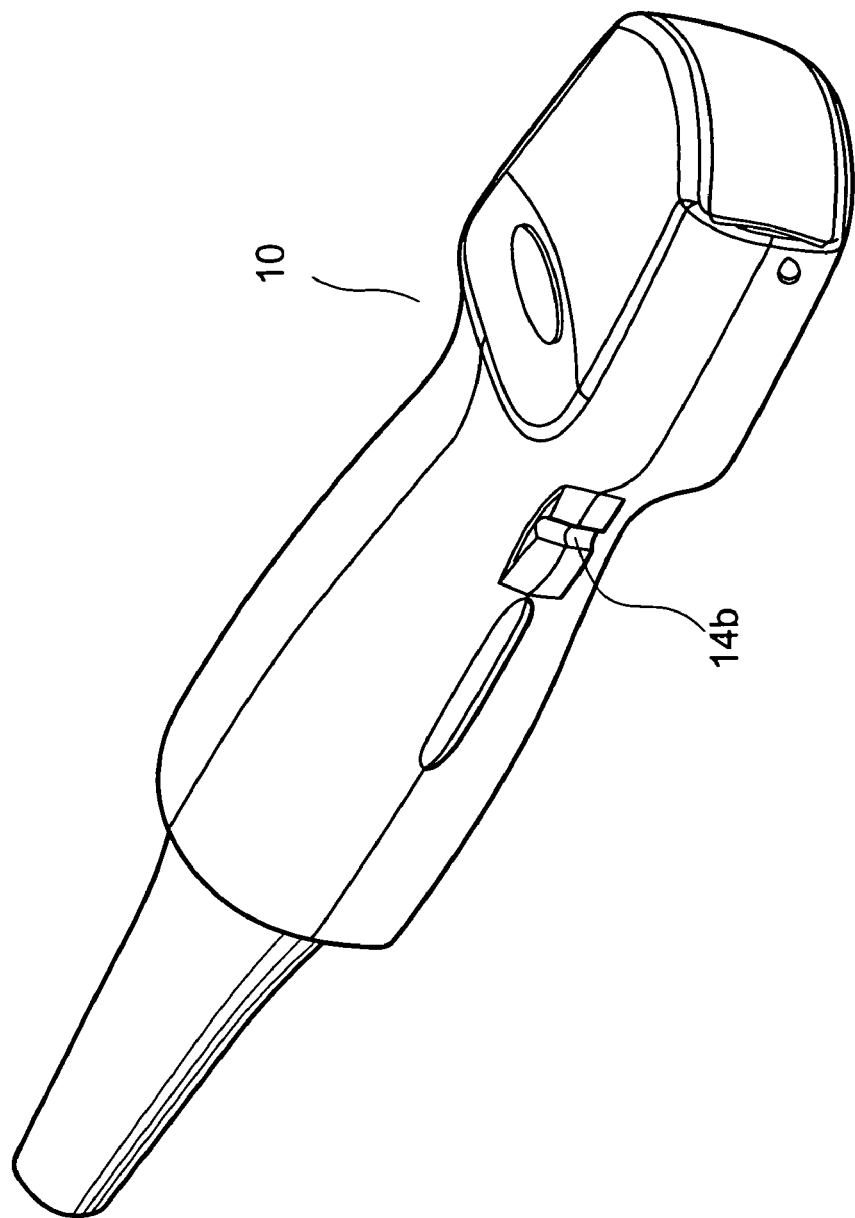
FIG. 7 is an illustration showing another exemplary view of the ultrasonic probe according to another embodiment.

FIG. 6 is an illustration showing an exemplary view of the ultrasonic probe 10 according to one embodiment. FIG. 7 is an illustration showing another exemplary view of the ultrasonic probe 10 according to one embodiment. FIG. 6 shows the ultrasonic probe 10 having a small notch 14a on its side surface. FIG. 7 shows the ultrasonic probe 10 having a small notch 14b on its opposite side surface. The notch 14a may be different from the notch 14b. The notches 14a and 14b may be the first mechanism. For example, the notches 14a and 14b are in an asymmetric position on each side of the ultrasonic probe 10. The paracentesis needle holder 20 has prongs (not shown in the drawings) which can engage the notches 14a and 14b. Such prongs may be the second mechanism. Since the notches 14a and 14b are in the asymmetric position, the paracentesis needle holder 20 can always be mounted on the ultrasonic probe 10 in a unique direction. Further, it could avoid the paracentesis needle holder 20 from loosening around the ultrasonic probe 10.

Alternatively, the ultrasonic probe 10 may have prongs instead of the notches 14a and 14b. The paracentesis needle holder 20 may have notches corresponding to the prongs of the ultrasonic probe 10. In addition, the notches 14a and 14b may be formed in different sizes or shapes, instead of the asymmetric positions. Three or more notches and corresponding prongs may be applied to accomplish the above purpose.

After the paracentesis needle holder 20 has been mounted on the ultrasonic probe 10, the ultrasonic probe 10 is contacted to the patient's body by the operator. The operator observes ultrasound images obtained in the scan by the ultrasonic probe 10 and confirms a position of a paracentesis operation target such as a diseased part. Once the target position is confirmed, the operator decides which size of the needle 90 to use. The adjustment screw 325 is winded counterclockwise so that the needle gutter unit 322 is lifted up towards the base 321. Accordingly, the spacing between the gutters 322a, 322b of the needle gutter unit 322 and the supporters 311a, 311b of the needle bearer 311 is widen enough for the determined needle 90 to be inserted along one of the gutters 322a and 322b as shown in FIG. 2. After the insertion, the adjustment screw 325 is then winded clockwise so that the needle gutter unit 322 is lowered towards the needle bearer 311. The spacing is adjusted appropriately to guide and allow the needle 90 to slide along the gutter 322a (322b). The operator penetrates the needle 90 up to the target along the gutter 322a (322b) and confirms a position of the penetrated needle 90 in the ultrasound images displayed in a monitor of an ultrasound diagnosis apparatus.

Figure 8:
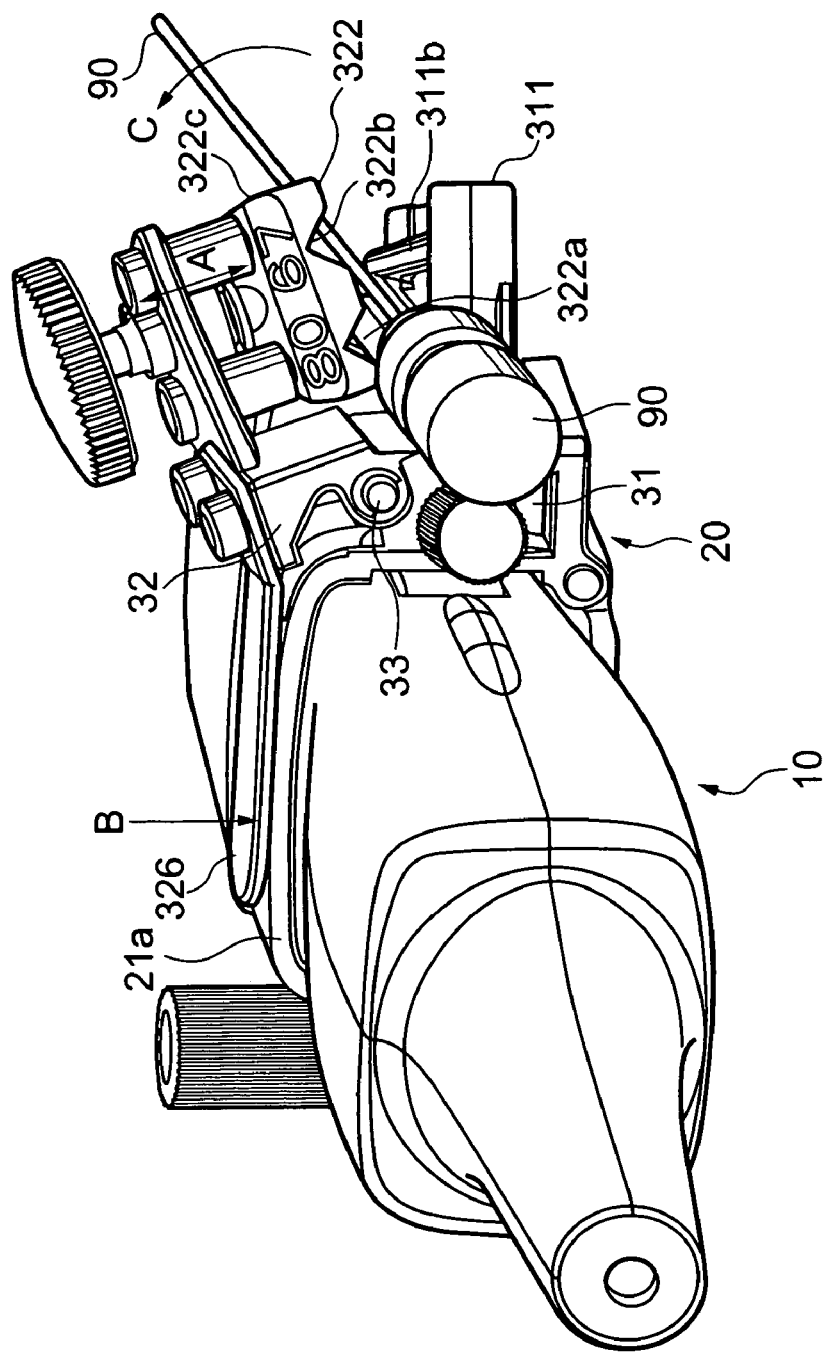
FIG. 8 illustrates the ultrasonic probe having the paracentesis needle holder particularly showing an example of a needle release according to one embodiment.
Figure 9:
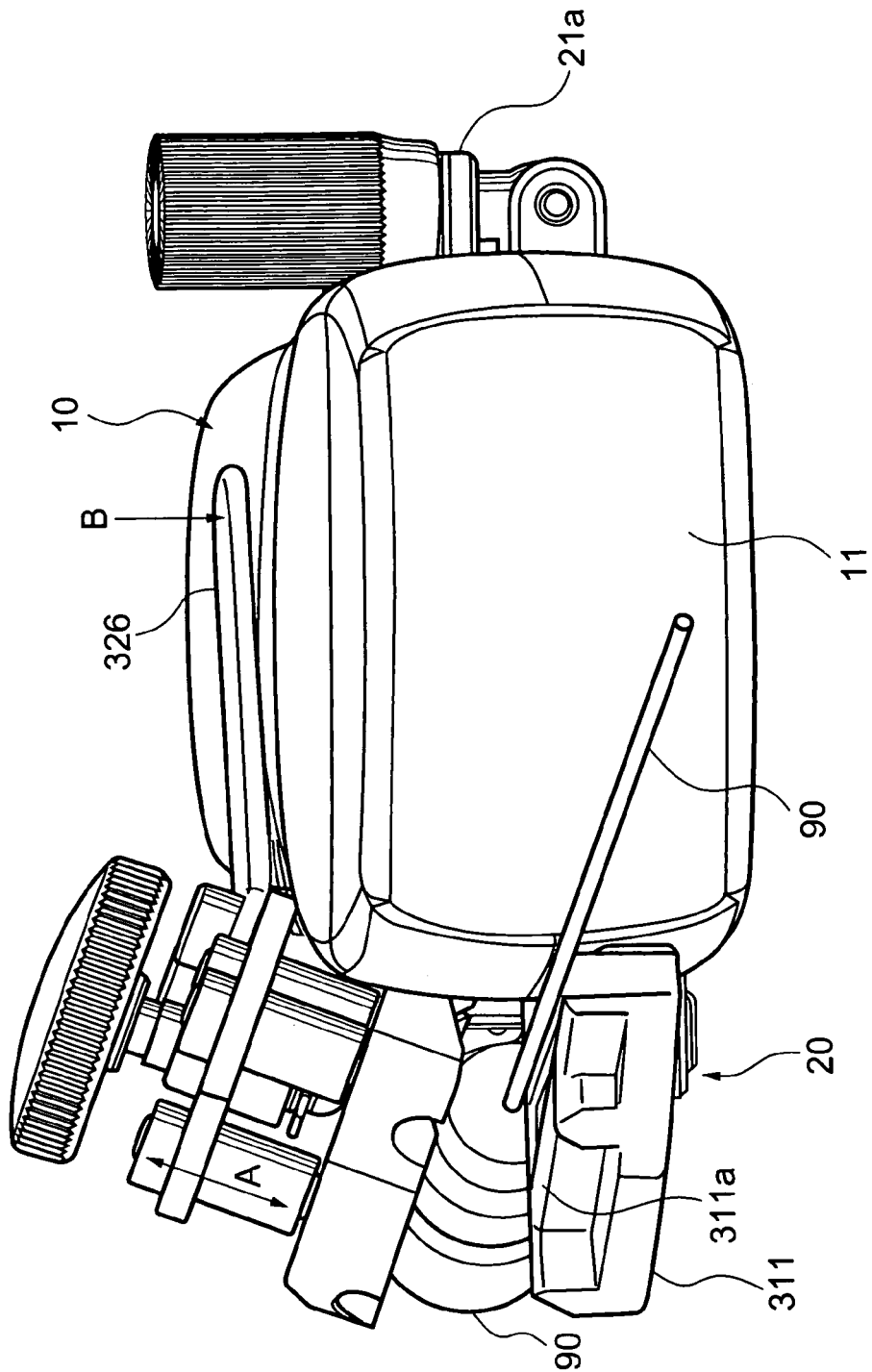
FIG. 9 illustrates the ultrasonic probe having the paracentesis needle holder particularly showing the needle release viewed from a side of an acoustic lens according to one embodiment.

When the operator recognizes the needle 90 has reached the target, the needle 90 may be released from the paracentesis needle holder 20 as shown in FIGS. 8 and 9. FIG. 8 illustrates the ultrasonic probe 10 having the paracentesis needle holder 20 particularly showing an example of a needle release according to one embodiment. FIG. 9 illustrates the ultrasonic probe 10 having the paracentesis needle holder 20 particularly showing the needle release viewed from a side of the acoustic lens 11 according to one embodiment.

The operator presses down the handle 326 towards the holder member 21a, that is, in a direction B. In response to the press-down, the guide unit 32 is turned around the hinge 33 as a turning axis in a direction C. The gutters 322a, 322b of the needle gutter unit 322 are released from the supporters 311a, 311b of the needle bearer 311. Accordingly, the ultrasonic probe 10 having the paracentesis needle holder 20 can be removed in the left direction in FIG. 8 or in the right direction in FIG. 9 while the needle 90 is penetrated in the patient's body. The operator then uses the independent needle 90 for obtaining target tissues inside the patient's body or injecting medical agents into the patient's body through the needle 90.

When there are two gutters 322a and 322b on the needle gutter unit 322, it would be clinically helpful if concrete guided angles are recognizable for the operator. Therefore, the angles to be guided by the gutters 322a and 322b may be displayed on a part of the needle gutter unit 322. The displayed angles may be angles against a horizontal direction of images to be displayed in the monitor of the ultrasound diagnosis apparatus. The angles are, for example, displayed on a surface 322c which is a part of the needle gutter unit 322 and above the gutters 322a and 322b. Each angle is displayed in a recognizable manner. As shown in FIG. 8, a display '80' above the gutter 322a represents an angle in degrees guided by the gutter 322a. Also, a display '67' above the gutter 322b represents an angle in degrees guided by the gutter 322b. Such angle difference may be understood as needles 91 and 92 in FIG. 1. The needle 91 guided by the gutter 322a is angled at 80 degrees from an horizontal line of ultrasound images obtained through a scan with ultrasound beams generated from the acoustic lens 11 when the images are displayed. Similarly, the needle 92 guided by the gutter 322b is angled at 67 degrees from the horizontal line. Therefore, the operator observes ultrasound images displayed in the monitor and determines which angle can be appropriate for the needle insertion. Based on the determination, the operator selects an appropriate one of the gutters 322a and 322b and inserts the needle 90 into the selected gutter 322a (322b). Therefore, the operator can easily conduct the paracentesis operation. The angles guided by the needle gutter unit 322 may be more than two angles according to the necessity. The angle display may alternatively be made on a part of the needle bearer 311 or anywhere as long as the guided angles are recognizable.

As described above, the guide unit 32 and the bear-up unit 31 are coupled by the hinge 33. The needle gutter unit 322 is usually biased towards the needle bearer 311 by the force of the spring provided at the hinge 33. Therefore, the operator can immediately and easily insert the needle 90 into one of the gutters 322a and 322b by pressing the handle 326 according to the necessity. For example, however, if the operator accidentally touches the handle 326, the handle 326 may happen to be pressed towards the holder member 21a, for example, during the needle insertion. This results in releasing the fit between the needle gutter unit 322 and the needle bearer 311. Therefore, the operator may not be able to accurately insert (or penetrate) the needle into the patient's body since the needle is unstable. In order to avoid such an undesired situation, the paracentesis needle holder 20 may be provided with a stopper mechanism which prevents the needle gutter unit 322 from turning in response to touching the handle 326.

Figure 10:
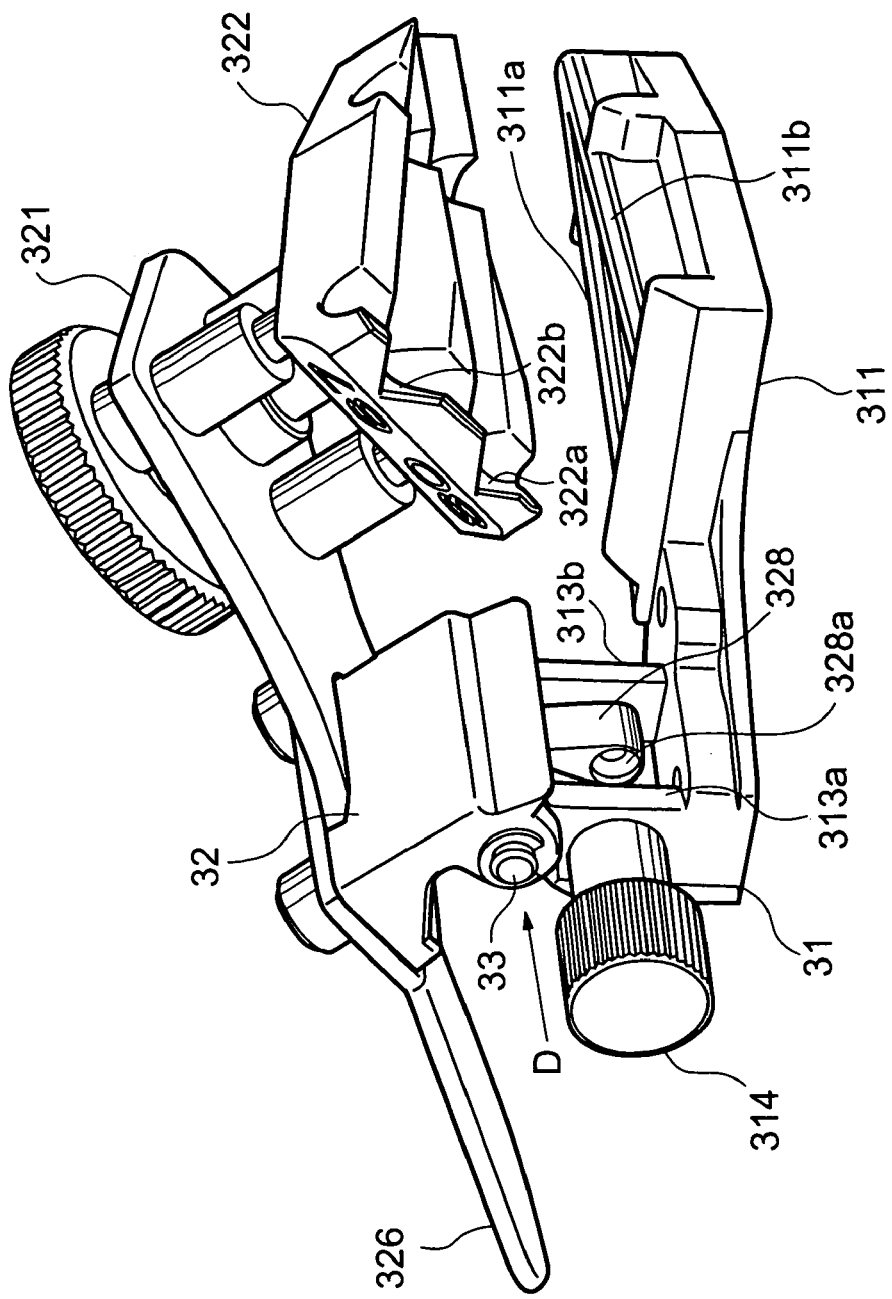
FIG. 10 is an illustration for explaining an exemplary stopper mechanism according to one embodiment.
Figure 11:
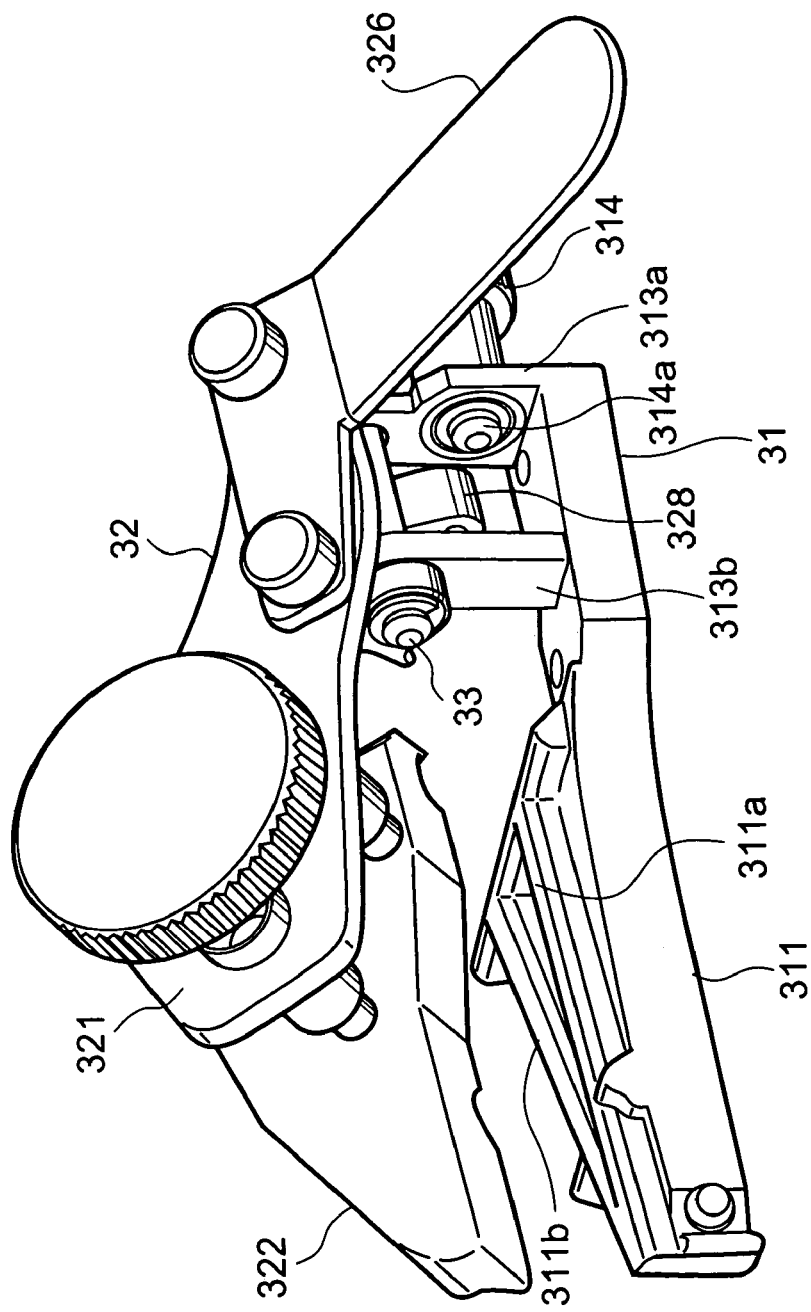
FIG. 11 illustrates the exemplary stopper mechanism of FIG. 10 viewed from another direction.

Such a stopper mechanism will be described with reference to FIGS. 9 to 11. FIG. 10 is an illustration for explaining an exemplary stopper mechanism according to the embodiments. FIG. 11 illustrates the exemplary stopper mechanism viewed from another direction.

In FIG. 10, the holder members 21a and 21b are omitted, and the needle gutter unit 322 is released from the needle bearer 311. As shown in FIG. 10, posts 313a and 313b are provided on the base of the bear-up unit 31 in an upward direction. The guide unit 32 is coupled to top ends of the posts 313a and 313b by the hinge 33. The guide unit 32 includes a prong 328 which bypasses the hinge 33 and has a through-hole 328a at its distal end. When the base 321 is pressed down towards the needle bearer 311, the through-hole 328a is positioned on an extension of an operative shaft 314a of a knob 314 while the needle gutter unit 322 and the needle bearer 311 are fitted each other.

Therefore, when the needle 90 is held in between one of the gutters 322a, 322b and one of the supporters 311a, 311b, the operator can push the knob 314 towards a direction D. In response, the operative shaft 314a is pushed out so as to be inserted into the through-hole 328a. Accordingly, since the guide unit 32 is locked relative to the bear-up unit 31, the guide unit 32 is prevented from turning even if the handle 326 is accidentally pressed towards the holder member 21a. That is, the needle 90 can always be locked and be kept stable as long as the operative shaft 314a is remained in the through-hole 328a. If the knob 314 is pulled out towards a direction opposite to the direction D, the operative shaft 314a is drawn back from the through-hole 328a and, accordingly, the needle 90 is unlocked and is ready to be released from the paracentesis needle holder 20.

For the above stop mechanism, the operative shaft 314a and the through-hole 328a may alternatively be screwed together by rotating the knob 314 so that the guide unit 32 can be fixed more stably to the bear-up unit 31. Accordingly, holding stability of the needle 90 can be improved and secured.

According to the embodiments described above, the needle 90 in various size of diameter can be guided in various angles. In addition, the paracentesis needle holder 20 can be made light and compact, and easily operated by the operator. Further, if all the materials constituting the paracentesis needle holder 20 are made of metals, it may be possible to sterilize the paracentesis needle holder 20 per se by boiling. Therefore, the operator can use the paracentesis needle holder 20 hygienically and safely.

Figure 12:
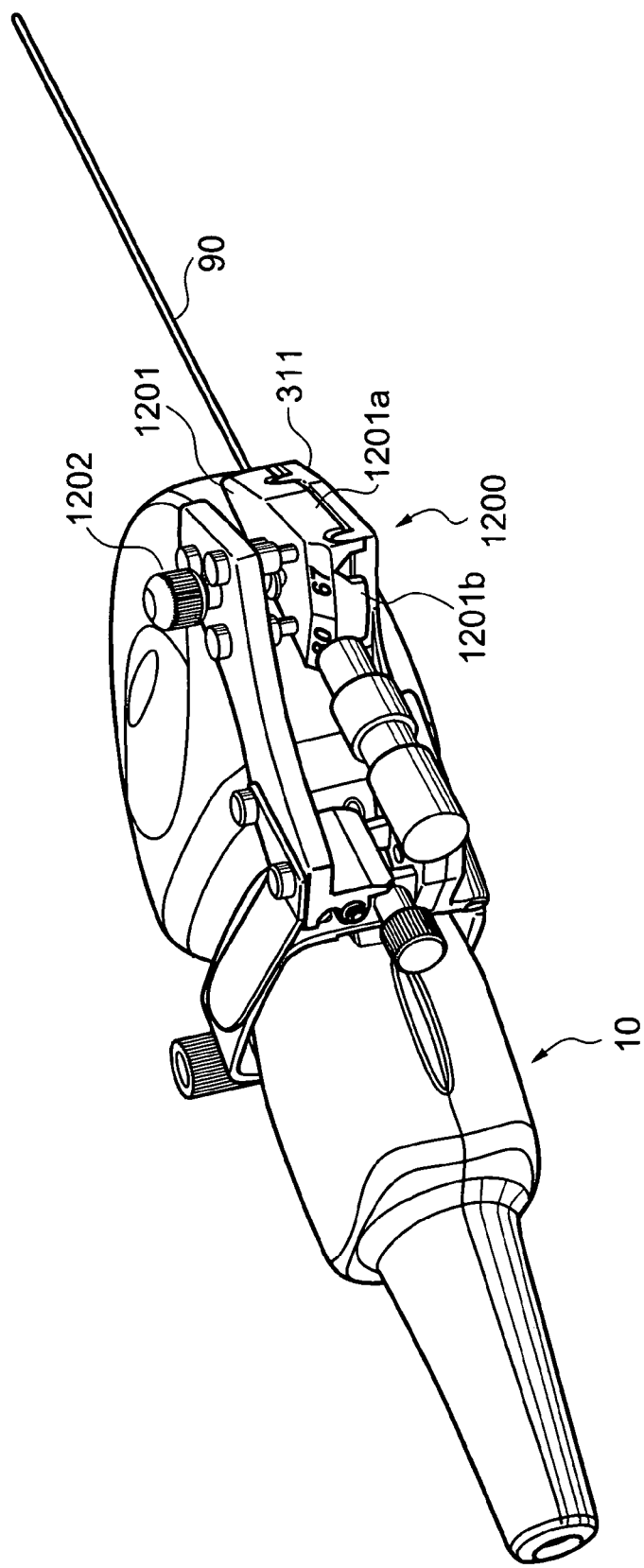
FIG. 12 illustrates a modified paracentesis needle holder mounted on the ultrasonic probe according to another embodiment.

A modification to the paracentesis needle holder 20 will be described with reference to FIG. 12. FIG. 12 illustrates an example of a modified paracentesis needle holder mounted on the ultrasonic probe 10 according to one embodiment. A paracentesis needle holder 1200 modified to the paracentesis needle holder 322 includes a needle gutter unit 1201 and an adjustment screw 1202, instead of the needle gutter unit 322 and the adjustment screw 325, respectively. The needle gutter unit 1201 has an extended outer side wall (or a distal wall) 1201a and an extended entrance side wall (or an entrance wall) 1201b. Compared to the side surfaces, for example, shown in FIG. 3, the extended outer side wall 1201a and the extended entrance side wall 1201b extend towards the needle bearer 311. Therefore, when the needle 90 is inserted into between the needle gutter unit 1201 and the needle bearer 311, the needle 90 can be prevented from deviating or coming out of the extended side surface 1201a, even if the operator inserts the needle 90 in a wrong direction (i.e., towards the extended side wall 1201a). Also, in the insertion, the needle 90 can be prevented from deviating from one of gutters of the needle gutter unit 1201, even if the operator accidentally gives a force to the needle 90 towards from the one gutter to the other gutter while the operator is holding the top of the needle 90. The extended entrance side surface 1201b may not be extended at a portion adjacent to the ultrasonic probe 10. Also, an inner side surface of the needle gutter unit 1201 facing the ultrasonic probe 10 may not extend towards the needle bearer 311. This is because the body of the ultrasonic probe works to prevent the needle 90 from deviating or coming out of the inner side surface. This modification may be advantageous particularly when the spacing between the needle gutter unit 1201 and the needle bearer 311 is not adjusted yet by the adjustment screw 1202 so that the needle 90 is easily inserted.

The adjustment screw 1202 is smaller in diameter than the adjustment screw 325. In addition, a head of the adjustment screw 1202 has a predetermined height and a round shape. This shape may be advantageous of preventing the adjustment screw 1202 from being winded as much as possible when a part of the operator's or patient's body contacts the adjustment screw 1202.

Finally, the paracentesis needle holder 20 according to the embodiments and a conventional type of a paracentesis needle holder will be compared in their needle positions relative to the ultrasonic probe. FIG. 13A illustrates a view of an exemplary relationship between the ultrasonic probe 10, the paracentesis needle holder 20, the needle 90, a radiated ultrasound 1300, and a patient's body 1301 according to one embodiment. Detailed elements of the paracentesis needle holder 20 are omitted in FIG. 13A. FIG. 13B is an illustration viewing the ultrasonic probe 10 mounting the paracentesis needle holder 20 from a side of the cable 13 according to the embodiments.

As shown in 13B, the paracentesis needle holder 20 faces to the ultrasonic probe 10 at the first side 1303 of the guide unit 32 and the second side 1304 of the bear-up unit 31 when paracentesis needle holder 20 is attached to (or mounted on) the ultrasonic probe 10. As shown in FIG. 13A, the ultrasonic probe 10 mounting the paracentesis needle holder 20 contacts a surface of the patient's body 1301. The needle 90 is inserted or penetrated into the patient's body 1301 under the guide of the paracentesis needle holder 20 while the ultrasound 1300 is radiated to the patient's body 1301. Since the needle 90 is guided close to the ultrasonic probe 10, only a little portion 1302 of the needle 90 is out of the radiated ultrasound 1300. In other words, the little portion 1302 of the needle 90 cannot be imaged by the ultrasound radiation. Such a range of the needle 90 like the little portion 1302 may be called a blind field.

Figure 14A:
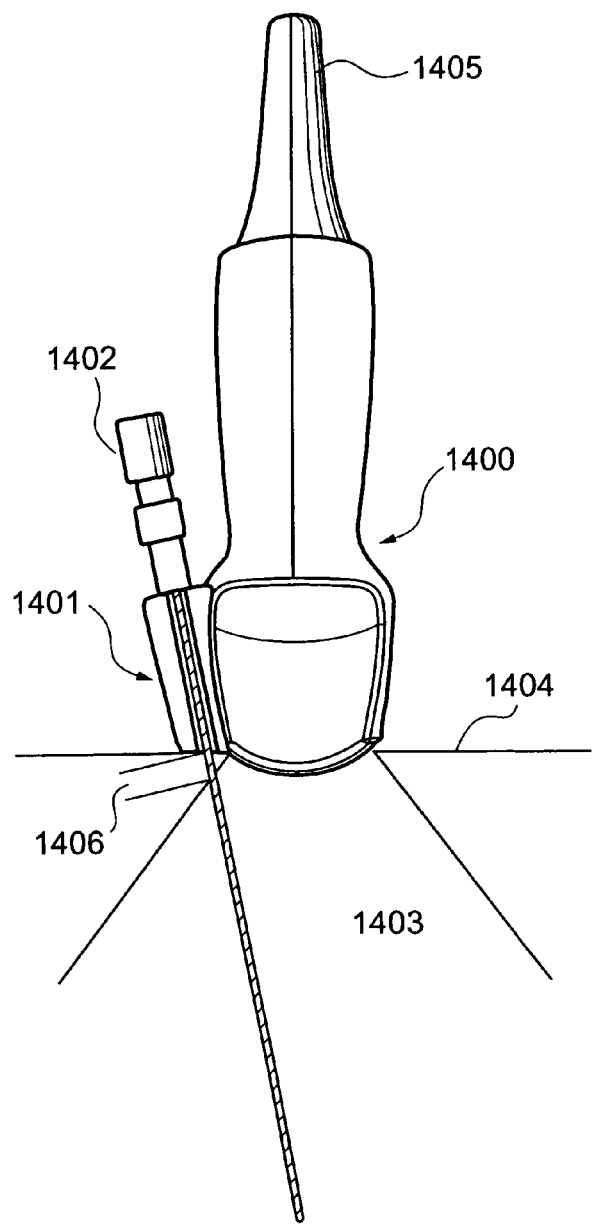
FIG. 14A illustrates one relationship between an ultrasonic probe, a needle holder, a needle, a radiated ultrasound, and a patient's body according to a prior art.
Figure 14B:
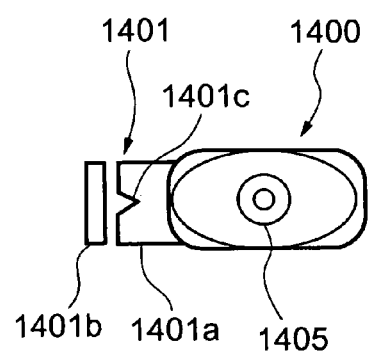
FIG. 14B is an illustration viewing the ultrasonic probe having the needle holder from a side of a cable according to the prior art.

Compared to FIGS. 13A and 13B, the conventional type of a paracentesis needle holder has a large blind field as shown in FIGS. 14A and 14B. FIG. 14A illustrates one known relationship between an ultrasonic probe 1400, a needle holder 1401, a needle 1402, a radiated ultrasound 1403, and a patient's body 1404. Detailed elements of the needle holder 1401 are omitted in FIG. 14A. FIG. 14B shows the known ultrasonic probe 1400 having the needle holder 1401 from a side of a cable 1405.

As shown in FIG. 14B, the needle holder 1401 includes a needle gutter unit 1401a and a needle bearer 1401b. The needle gutter unit 1401 has a gutter 1401c at a distal end from the ultrasonic probe 1400. The needle 1402 (not shown in FIG. 14B) is guided by the gutter 1401c and held by the needle gutter unit 1401a and the needle bearer 1401b. Since the needle 1402 is not guided close to the ultrasonic probe 1400 because of the thickness of the needle gutter unit 1401a, quite a large portion 1406 of the needle 1402 is out of the radiated ultrasound 1403. In other words, the large portion 1406 of the needle 1402 cannot be imaged by the ultrasound radiation.

Therefore, the paracentesis needle holder 20 can reduce the blind field, compared to the conventional needle holder 1401. The reduced blind field may help the operator to conduct the needle insertion more accurately.

The embodiments described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. A paracentesis needle holder attachable to an ultrasonic probe, the holder comprising:
   a needle guide, including a pivotable first base and a non-pivotable second base, configured to guide a needle in a plurality of directions between the first and second bases;
   an adjustment mechanism provided at the needle guide and configured to adjust spacing between the first base and the second base in accordance with a diameter of the needle;

an open/close mechanism coupled with the needle guide and configured to close the first and second bases by pivoting the pivotable first base so that the needle is guided in one of the directions and to open the first and second bases so that the needle becomes releasable from the holder;

said pivotable first base has a surface including gutters corresponding to the plurality of directions;

said pivotable first base is pivotably moveable from said non-pivotable second base by a hinge;

said adjustment mechanism being coupled to said pivotable first base member; and, said adjustment mechanism extending in a direction perpendicular to a surface of said pivotable first member that is opposite to the surface containing said gutters.

2. The holder according to claim 1, wherein the needle is placed along one of the gutters.

3. The holder according to claim 2, wherein angle information of the plurality of directions is displayed on the needle guide for each of the gutters.

4. The holder according to claim 1, wherein the open/close mechanism includes a stopper mechanism configured to prevent the open/close mechanism from opening the first and second bases.

5. The holder according to claim 1, wherein the pivotable first base has a side wall and the pivotable first base and the non-pivotable second base are opposed to each other when the first and second bases are closed, and at least a part of the side wall is extended towards the non-pivotable second base.

6. The holder according to claim 5, wherein the side wall is a distal wall of the first base.

7. The holder according to claim 5, wherein the side wall is an entrance wall of the first base.

8. The paracentesis needle holder of claim 1, wherein the hinge extends along its length generally in the same direction as the needle.

9. A paracentesis needle holder attachable to an ultrasonic probe, the holder comprising:

a holder member attachable around the ultrasonic probe; a fixed member attached to the holder member and configured to have a needle bearer; a pivoted member coupled to the fixed member and configured to have a surface including a gutter unit, the pivoted member being biased to the fixed member by a bias member; an adjustment mechanism provided in said paracentesis needle holder and configured to adjust spacing between the first base and the second base in accordance with a diameter of the needle, a handle attached to the pivoted member and configured to turn the pivoted member against a force of the bias member and to open the pivoted member and the fixed member; the gutter unit and the needle bearer are configured to face to each other and to guide a needle in a plurality of directions; said adjustment mechanism being coupled to said pivoted member; and, said adjustment mechanism extending in a direction perpendicular to a surface of said pivoted member that is opposite to the surface containing said gutter unit.

10. The paracentesis needle holder of claim 9, wherein the bias member is a hinge, wherein the hinge extends along its length generally in the same direction as the needle.

11. A paracentesis needle holder for an ultrasonic probe, the holder comprising: a guide unit configured to have a surface including a gutter unit with a gutter portion capable of holding a needle at a plurality of angles with respect to the ultrasonic probe; a bear-up unit coupled to the guide unit and configured to have a needle bearer with a support member, the gutter portion and the supporter member being configured to securely hold the needle in place when the guide unit and the bear-up unit are closed; an adjustment mechanism provided to said guide unit and configured to adjust spacing between the gutter portion and the needle bearer when the guide unit and the bear-up unit are closed; said adjustment mechanism being coupled to said guide between said guide unit and said bear-up unit; and, said adjustment mechanism extending in a direction perpendicular to a surface of said guide unit that is opposite to the surface containing said gutter portion.

12. The paracentesis needle holder of claim 11, wherein the guide unit is pivotably coupled to the bear-up unit by a hinge, wherein the hinge extends along its length generally in the same direction as the needle.

13. An ultrasonic probe comprising: a main unit; and a paracentesis needle holder mounted onto the main unit, the paracentesis needle holder including: a needle guide, including a first base and a second base, configured to guide a needle in a plurality of directions between the first and second bases; said first base configured to have a surface including a gutter unit; an adjustment mechanism provided at the needle guide and configured to adjust spacing between the first base and the second base in accordance with a diameter of the needle; and an open/close mechanism coupled with the needle guide and configured to close the first and second bases so that the needle is guided in one of the directions and to open the first and second bases so that the needle becomes releasable from the holder; and said adjustment mechanism being coupled to said first base; and, said adjustment mechanism extending in a direction perpendicular to a surface of said first base that is opposite to the surface containing said gutter unit.

14. The probe according to claim 13, further comprising a first mechanism provided at the main unit and a second mechanism provided at the paracentesis needle holder, wherein the first and second mechanisms are fitted to each other so that the paracentesis needle holder is mounted on the main unit.

15. The paracentesis needle holder of claim 13, wherein the first base is pivotably moveable from the second base by a hinge, wherein the hinge extends along its length generally in the same direction as the needle.

16. An ultrasonic probe comprising: a main unit; a holder member attached around the main unit; a fixed member attached to the holder member and configured to have a needle bearer; a pivoted member coupled to the fixed member and configured to have a surface including a gutter unit, the pivoted member being biased to the fixed member by a bias member; an adjustment mechanism provided at the needle guide and configured to adjust spacing between the pivoted member and the fixed member in accordance with a diameter of the needle; a handle attached to the pivoted member and configured to turn the pivoted member against a force of the bias member and to open the pivoted member and the fixed member, wherein the gutter unit and the needle bearer are configured to face to each other and to guide a needle in a plurality of directions; said adjustment mechanism being coupled to said pivoted member; and, said adjustment mechanism extending in a direction perpendicular to a surface of said pivoted member that is opposite to the surface containing said gutter unit.

17. The probe according to claim 16, further comprising a first mechanism provided at the main unit and a second mechanism provided at the holder member, wherein the first and second mechanisms are fitted to each other so that the holder member is mounted on the main unit.

18. The paracentesis needle holder of claim 16, wherein the bias member is a hinge, wherein the hinge extends along its length generally in the same direction as the needle.

19. An ultrasonic probe comprising: a main unit; and a paracentesis needle holder mounted onto the main unit, the paracentesis needle holder including: a needle guide configured to have a surface including a gutter unit with a gutter portion capable of holding a needle at a plurality of angles with respect to the ultrasonic probe; said needle guide including a first base having a first side and a second base having a second side, configured to guide a needle in at least one direction between the first and second bases, the first and second bases being opposed to each other when the first and second bases are closed, the first and second bases facing to the ultrasonic probe at the first and second sides along a proximal end to a distal end of the ultrasonic probe when the first and second bases are closed; an adjustment mechanism provided at the needle guide and configured to adjust spacing between the first base and the second base in accordance with a diameter of the needle; an open/close mechanism coupled with the needle guide and configured to close the first and second bases so that the needle is guided in one of the at least one direction and to open the first and second bases so that the needle becomes releasable from the paracentesis needle holder; and said adjustment mechanism being coupled to said first base; and, said adjustment mechanism extending in a direction perpendicular to a surface of said first base that is opposite to the surface containing said gutter unit.

20. The ultrasonic probe of claim 19, wherein the first base is pivotably moveable from the second base by a hinge, wherein the hinge extends along its length generally in the same direction as the needle.

\* \* \* \* \*